United States Patent [19]

Kolenik et al.

[11] 4,181,133
[45] Jan. 1, 1980

[54] PROGRAMMABLE TACHYCARDIA PACER

[75] Inventors: Steve A. Kolenik, Leechburg; Robert A. Walters, Murrysville, both of Pa.

[73] Assignee: Arco Medical Products Company, Leechburg, Pa.

[21] Appl. No.: 907,659

[22] Filed: May 22, 1978

[51] Int. Cl.² ............................................ A61N 1/36
[52] U.S. Cl. .......................... 128/419 PG; 128/419 D
[58] Field of Search ..................... 128/419 PG, 419 D

[56] References Cited

U.S. PATENT DOCUMENTS

| Re. 27,757 | 9/1973 | Mirowski | 128/419 D |
|---|---|---|---|
| 3,857,398 | 12/1974 | Rubin | 128/419 D |
| 3,937,226 | 2/1976 | Funke | 128/419 D |
| 3,939,844 | 2/1976 | Pequignot | 128/419 PG |
| 3,942,534 | 3/1976 | Allen | 128/419 PG |
| 4,049,004 | 9/1977 | Walters | 128/419 PG |

OTHER PUBLICATIONS

Fisher et al., "American Journal of Cardiology", vol. 41, pp. 94–102, Jan. 1978.

Primary Examiner—William E. Kamm
Attorney, Agent, or Firm—John C. Martin, Jr.

[57] ABSTRACT

A programmable implantable pacer is provided for performing the dual functions of demand pacing as well as standby tachycardia breakup. A command parameter control is used for programmably controlling parameters of the pacer operation as well as of the tachycardia recognition and response to same. Upon recognition of tachycardia, a series of stimulus pulses of predetermined rate and number are delivered, the tachycardia breakup pulses being generated and delivered through an output circuit utilized commonly with the demand pacer circuitry.

10 Claims, 2 Drawing Figures

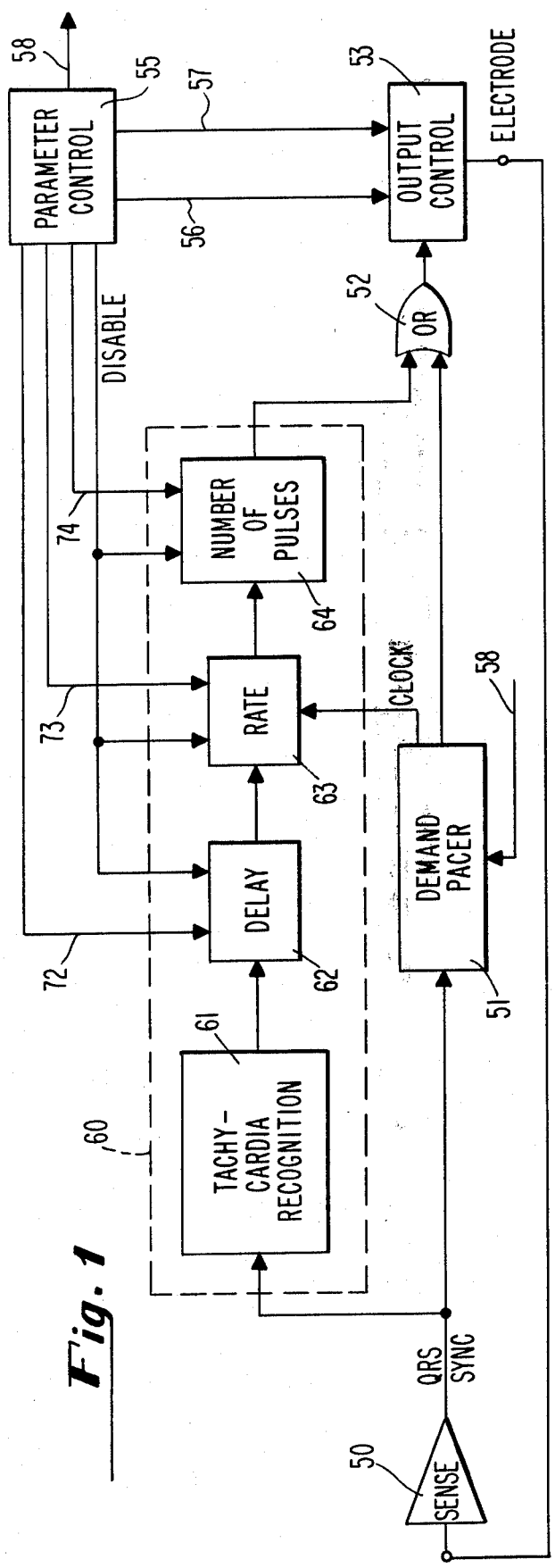

PROGRAMMABLE TACHYCARDIA PACER

BACKGROUND OF THE INVENTION

This invention lies in the area of cardiac pacing apparatus and, more particularly, apparatus for combining cardiac pacing and arrhythmia detection and arrest functions in the same device.

Present day pacers are all designed to treat the condition of bradycardia, i.e., an abnormally low natural heart rate. The demand type pacer is an excellent response to this condition, being adapted to provide stimulus pulses when and only when the natural rate drops below a predetermined level. At the same time, there has developed an awareness of the need for an implantable device which supplements the pacing function with a cardiac defibrillator (U.S. Pat. No. 3,857,398) or some other form of arrhythmia prevention and/or arrest apparatus. In the care of arrhythmia or tachycardia, the condition is that of too high a natural rate. Because of the different nature of the problems encountered in dealing with these two different conditions, the circuitry adopted for treating them is distinct. In prior art devices designed to treat both conditions, generally a first set of electrodes is utilized for delivering cardiac pacing signals, and a second pair of electrodes is utilized for delivering defibrillator or tachycardia breakup pulse signals. Further, the circuits for generating these different signals are totally independent of each other.

As used herein, the term tachycardia means a heartbeat at a rate which is abnormally high and accordingly considered to be dangerous if permitted to continue, or any arrhythmia involving recognizable heartbeat patterns containing repetitions which are in excess of a periodic heartbeat within a safe range.

SUMMARY OF THE INVENTION

It is an object of this invention to provide a method, and implantable apparatus for carrying out such method, of automatically treating the condition of tachycardia by the use of applied electrical pulses of the same form as used for pacing a patient.

It is another object of this invention to provide a programmable device for programming the operating parameters in the detection and control of tachycardia.

It is another object of this invention to provide an improved implantable device for providing the combined functions of cardiac pacing and tachycardia detection and control, which improved device utilizes common programming and output control circuits.

It is another object of this invention to provide an implantable device for cardiac pacing and tachycardia detection and control, while device utilizes digital techniques in programming its operation and in providing output pulses.

It is another object of this invention to provide a system utilizing batch programming of both a demand pacer operation and the operation of tachycardia detection and control.

In accordance with the above objects, there is disclosed a programmable device, suitably implantable in a human patient, adapted to provide the operations of both demand cardiac pacing and also tachycardia detection and control. The device incorporates programmable control means for controlling the operating parameters of the pacer operation, as well as at least one variable of the generated tachycardia timing signals. Common programmable output means are utilized for delivering a common stimulus and tachycardia signal to the patient for the purposes of pacing and tachycardia breakup respectively.

BRIEF DESCRIPTION OF THE DRAWINGS

FIG. 1 is a block diagram showing the functional arrangement of the apparatus of this invention, as well as the method of providing the combined operations of pacing and tachycardia recognition and control.

FIG. 2 is a block schematic diagram of a circuit for carrying out the functions of tachycardia recognition and development of control signals for delivering tachycardia breakup pulses to the patient.

DESCRIPTION OF THE PREFERRED EMBODIMENT

The invention of this application is embodied in a digital apparatus which is externally programmable. A pacer incorporating such digital programming features is disclosed in U.S. Pat. No. 4,049,004, "Implantable Digital Cardiac Pacer Having Externally Selectable Operating Parameters and 'One Shot' Digital Pulse Generator For Use Therein", which patent is incorporated herein by reference. The referenced patent shows in detail a digital type cardiac pacer, having a master parameter control arrangement to provide control of a number of pacer operating parameters as a function of an externally provided program signal. Among the pacer operating parameters which are thus programmable are stimulation pulse interval, stimulation pulse width, stimulation pulse amplitude, pacer sensitivity, pacer refractory period, and pacer mode (demand or asynchronous). The master parameter control, as disclosed in the referenced patent, performs the functions of receiving the external program signal and generating control signals derived therefrom for control of the operating parameters. It is suitably packaged on one chip, and has sufficient flexibility to be adapted to simultaneously control different or additional operating parameters. In the embodiment of this invention, the master parameter control circuit is utilized additionally to control operating parameters, or variables, of the circuitry which performs the functions of tachycardia recognition and generation of tachycardia breakup signals. While use of the parameter control chip is desirable from the standpoint of efficiency, it is understood that the control functions may be performed with any equivalent circuitry.

Referring to FIG. 1, the functional components of the apparatus of this invention are illustrated in block diagram form. Elements 50, 51 and 53 incorporate the elements of the cardiac pacer of referenced U.S. Pat. No. 4,049,004, except for the parameter control circuitry. Block 51, titled Demand Pacer, includes all of the circuitry necessary for carrying out the normal functions of a demand pacer, including the demand logic and generation of the pacer stimulus timing signal. For the digital embodiment of block 51, a relatively high frequency clock circuit is provided from which all timing operations are derived. A clock output from block 51 is shown as connected to the tachycardia portion 60. Parameter control 55 provides a plurality of outputs designated schematically on the single line 58, which outputs are inputted to demand pacer 58 for control of some of the pacer parameters enumerated above. The detected heartbeats are sensed at the electrode and inputted to sense circuit 50, which is suitably a sense amplifier having a controllable sensitivity, and which outputs a QRS sync signal in response to the detection of a QRS signal. This is inputted to the demand pacer, for the conventional purpose of resetting the timing circuitry.

The timing signals from the demand pacer portion 51 are transmitted through OR gate 52 to circuitry which performs the output control functions, as designated at block 53. In practice, block 53 contains a circuit for receiving clock pulses from the clock generator, suitably dividing such clock pulses, and using the divided clock pulses as an input to a width control circuit. The width control circuit additionally receives an input control signal on line(s) 56 from parameter control 58. For example, the width of the output pulses may be controlled to time periods of approximately 0.5 ms, 1.0 ms, and 2.0 ms, or any other suitable time periods. The output control function 53 also incorporates circuitry for controlling the amplitude, which circuitry receives a parameter control signal on line(s) 57 generated at parameter control block 58. While this signal may be controlled to any desired level, it is suitably current controlled to levels of, for example, 8 and 10 ma. Circuitry for providing both pulse width and pulse level control are disclosed in detail in the referenced U.S. Pat. No. 4,049,004.

The QRS sync signal is also inputted to block 60, which contains block designating different functions to be performed in generating tachycardia breakup signals. Block 61, labeled TACHYCARDIA RECOGNITION, provides for recognizing the existence of a heartbeat which is sufficiently high to indicate tachycardia. The conventional technique for tachycardia recognition, as provided in the prior art, is that of measuring detected QRS pulse rate against a predetermined limit, e.g., 200 bpm. A conventional pulse rate detector is utilized, with threshold logic connected to the output of the pulse rate detector to produce an output pulse when the pulse rate of the heart exceeds a predetermined average rate over the course of a specified number of heartbeats.

Upon recognition of tachycardia, it is necessary to introduce a delay of a predetermined time period following the last detected heartbeat. The delay is introduced at block 62, labeled DELAY, and may vary, for example, from 50 ms to 550 ms, in a predetermined number of discrete steps. The delay is programmable, and is controlled by a signal on line 72 from parameter control block 55.

The next function indicated is shown as RATE in block 63, and is programmable by control signals connected on line 73 from parameter control block 55. By rate of the tachycardia breakup pulses is meant the rate at which a series of such pulses is delivered. Such rate may suitably be within a range of 200 to 300 pulses per second, and suitably 4 discrete rates are available. These numbers are illustrative only, it being understood that the programmed rates will be chosen in accordance with understandings of what rates have the optimum efficacy in terminating ventricular tachycardia.

The next function is indicated at block 64 as NUMBER OF PULSES. This function likewise is programmable by control signals connected on line 74 from parameter control block 55. By number of pulses is meant the actual number of breakup pulses delivered following the delay. For example, this number is suitably programmed to be 1, 2, 4 or 8.

In addition, each of these functions may be disabled by a signal connected from the parameter control block 55. If the entire tachycardia circuit 60 is disabled, then the unit operates strictly as a demand pacer. Given the determination of delay, rate, and number of pulses, the breakup pulses thus generated are inputted to OR gate 52 and thence to output control block 53, for subsequent delivery to the electrode. Thus, the tachycardia breakup pulses, independently of their number and rate, and in turn programmed as to pulse width and amplitude at output control block 53, the same as the pacing stimulus pulses generated by the demand pacer portion of the apparatus.

Referring now to FIG. 2, there is shown a detailed block diagram of circuitry adapted for use in generating tachycardia breakup pulses and carrying out the functions shown within block 60 of FIG. 1. The QRS sync signal is inputted both to a QRS rate detector 66 and to an AND gate 67. Rate detector 66 detects the existence of QRS signals which occur at a rate exceeding a predetermined limit for a predetermined length of time. This may, for example, be 20 pulses at an average rate of 150 ppm or greater. Circuits for accomplishing this function are well known in the art and readily available. The output of rate detector 66 is inputted as a first input to AND gate 67, the second input to gate 67 being the QRS sync signal. By this device, as soon as the rate detector makes the determination that a state of tachycardia exists, AND gate 67 is enabled. However, no output is produced from the gate until the next QRS snyc signal, so as to provide synchronization of the subsequent circuitry timewise with respect to the patient's heartbeat. The output from AND gate 67 is also connected back to reset the QRS rate detector 66. The output from AND gate 67 is connected to a delay one shot circuit 62, for producing a delay of a predetermined time period. The delay may be programmed by signals on line 72 from parameter control block 55. Circuit 62 is, for the present embodiment, suitably a digital one shot generator, such as disclosed in referenced U.S. Pat. No. 4,049,004, but may be any other type of equivalent one shot signal. At the close or end of the one shot signal, an output is connected through to the duration monostable multivibrator circuit 68. This circuit is designed to produce a timing signal which, for example, goes to a logic 1 at the end of the delay, and stays as a logic 1 for a predetermined time period which is controlled by control signals on line 74. This logic signal is gated at AND gate 76 along with timing signals from rate control circuit 71. Circuit 71 in turn receives clock pulses from the clock generator within demand pacer block 51, and divides same by a predetermined factor which is controlled by signals on line 73 from control block 55. Such division is performed by standard circuits, e.g., a plural stage digital counter which receives inputted clock pulses and produces an output when a selected stage or combination of stages attains a predetermined logic level, following which the counter is reset and the cycle is repeated. Thus, the output from rate control circuit 71 is a periodic pulse signal at a rate which is a function of the initial clock pulse rate and the dividing factor introduced in circuit 71. In turn, the output of gate 76 is a series of predetermined number of pulses designed as tachycardia breakup timing pulses. The first pulse of the series has been delayed relative to the last sensed QRS signal; the series of timing pulses has a rate as determined by rate control circuit 71; and the series consists of a number of pulses which is a function of the duration of the enabling signal as established by circuit 68. These signals are inputted to OR gate 52, and are modified by output control circuits 53 in the manner heretofore described to produce output pulses.

From the above, it is seen that there is provided apparatus which meets the objects as set forth above. The same type of pulses as produced by the common output control circuit 53 are used both for the operations of pacing and for tachycardia breakup. Thus, a common control channel is used for producing both types of pulses, which common control channel in turn is controlled by the master parameter control circuit. This arrangement enables batch programming of both the demand pacer and tachycardia operating parameters, whereby a single control word, such as a 10 bit word is transmitted to the master parameter control, and it in turn transmits appropriate control signals to the demand pacer and tachycardia portions of the apparatus. The apparatus has been illustrated as providing for programmable control of delay, rate and number of pulses for the tachycardia breakup operation, but it is to be understood that additional control variations may be accomplished with state of the art logic techniques.

We claim:

1. Programmable apparatus adapted for implantation in a patient, and providing the dual functions of cardiac pacing and delivery of tachycardia breakup pulses upon occurrence of tachycardia in said patient, comprising:
   a. pacing means for providing pacing timing signals in the absence of natural patient heartbeats, said pacing means including a clock generator which generates clock pulses independently of patient heartbeat signals;
   b. means for detecting the condition of tachycardia in said patient;
   c. tachycardia means for generating tachycardia timing signals in response to said detected tachycardia, said tachycardia means being connected to said pacing means and generating said tachycardia timing signals from said clock pulses;
   d. programmable control means for controlling at least one variable of said tachycardia timing signals and for generating output control signals; and
   e. common programmable output means connected to receive said pacing timing signals and said tachycardia timing signals, and connected to be controlled by said output control signals, for generating and delivering to said patient output pulses in response to each of such timing pulses.

2. The apparatus as described in claim 1, wherein said common programmable output means receives output control signals from said programmable control means for controlling pulse width and pulse amplitude.

3. The apparatus as described in claim 1, wherein said programmable control means provides control signals connected to said tachycardia timing means for controlling the rate of said tachycardia timing signals.

4. The apparatus as described in claim 1, wherein said programmable control means provides a control signal connected to said tachycardia timing signal means for controlling the number of pulses produced in response to detected tachycardia.

5. The apparatus as described in claim 1, wherein said tachycardia detecting means comprises a circuit for providing a tachycardia recognition signal synchronized with the occurrence of a patient QRS signal.

6. The apparatus as described in claim 5, wherein said programmable control means provides a control signal for introducing a predetermined delay between said tachycardia recognition signal and the initial time of generating tachycardia timing signals in response to detected tachycardia.

7. The apparatus as described in claim 1, wherein said programmable control means is adapted to receive parameter control data in the form of a multiple bit data word transmitted from an external source, said data word containing data for control of said tachycardia means and said common programmable output means.

8. The apparatus as described in claim 1, wherein said programmable control means is adapted to receive parameter control data in the form of a multiple bit data word transmitted from an external source, said data word containing data for controlling at least one parameter of said pacing timing signals and at least one parameter of said tachycardia timing signals.

9. Programmable apparatus adapted for implantation in a patient, and providing the dual functions of cardiac pacing and delivery of tachycardia breakup pulses upon occurrence of tachycardia in said patient, comprising:
   a. pacing means for providing pacing timing signals in the absence of natural patient heartbeats, said pacing means including a clock generator which generates clock pulses independently of patient heartbeat signals;
   b. recognition means for sensing patient QRS signals and detecting tachycardia in said patient, said recognition means providing a recognition signal which is initiated concurrently with the occurrence of a patient QRS signal;
   c. tachycardia means enabled by said recognition signal for generating tachycardia timing signals in response to said detected tachycardia, said tachycardia means being connected to said pacing means and generating said tachycardia timing signals from said clock pulses;
   d. programmable control means for controlling at least one variable of said tachycardia timing signals and for generating output control signals; and
   e. common programmable output means connected to receive said pacing timing signals and said tachycardia timing signals, and connected to be controlled by said output control signals, for generating and delivering to said patient output pulses in response to each of such timing pulses.

10. The apparatus as described in claim 9, wherein said recognition means comprises input means for receiving detected patient QRS signals, a QRS rate detector for determining the rate of successive QRS signals and providing an output when said rate exceeds a predetermined value, a gate circuit receiving said rate detector output and patient QRS signals as inputs and providing said enabling recognition signal only upon the occurrence of both of said inputs.

* * * * *